(12) United States Patent
Delmotte (10) Patent No.: US 7,766,919 B2
(45) Date of Patent: Aug. 3, 2010

(54) DEVICES FOR MIXING AND EXTRUDING MEDICALLY USEFUL COMPOSITIONS

(75) Inventor: Yves Delmotte, Neufmaison (BE)

(73) Assignees: Baxter International Inc., Deerfield, IL (US); Baxter Healthcare, Glattpark (Opfikon) (CH)

(*) Notice: Subject to any disclaimer, the term of this patent is extended or adjusted under 35 U.S.C. 154(b) by 696 days.

(21) Appl. No.: 11/555,942

(22) Filed: Nov. 2, 2006

(65) Prior Publication Data

US 2008/0109002 A1 May 8, 2008

Related U.S. Application Data

(63) Continuation of application No. 10/265,076, filed on Oct. 4, 2002, now Pat. No. 7,135,027.

(51) Int. Cl.
*A61B 17/58* (2006.01)
(52) U.S. Cl. .................. 606/93; 606/92; 606/94
(58) Field of Classification Search ............ 606/92, 606/93, 94; 604/191, 82, 85, 89; 424/94.64, 424/443, 423
See application file for complete search history.

(56) References Cited

U.S. PATENT DOCUMENTS

| | | | |
|---|---|---|---|
| 2,533,004 A | 5/1950 | Ferry et al. |
| 2,576,006 A | 11/1951 | Ferry et al. |
| 3,523,807 A | 8/1970 | Gerendas |
| 3,641,240 A | 2/1972 | Hymes et al. |
| 3,723,244 A | 3/1973 | Breillatt, Jr. |
| 4,016,877 A | 4/1977 | Cruz, Jr. et al. |
| 4,061,787 A | 12/1977 | Higgins |
| 4,225,580 A | 9/1980 | Rothman et al. |
| 4,238,480 A | 12/1980 | Sawyer |
| 4,359,049 A | 11/1982 | Redl et al. |
| 4,442,655 A | 4/1984 | Stroetmann |
| 4,463,875 A | 8/1984 | Tepic |
| 4,505,817 A | 3/1985 | Blomback et al. |
| 4,505,822 A | 3/1985 | Blomback et al. |
| 4,537,767 A | 8/1985 | Rothman et al. |
| 4,548,736 A | 10/1985 | Muller et al. |

(Continued)

FOREIGN PATENT DOCUMENTS

DE 3443167 A1 11/1984

(Continued)

OTHER PUBLICATIONS

Baker, et al., "Mediastinal Fibrin Glue: Hemostatic Effect and Tissue Response in Calves", Ann. Thorac. Surg., 47, 450-52 (1989).

(Continued)

*Primary Examiner*—Pedro Philogene
(74) *Attorney, Agent, or Firm*—Marshall, Gerstein & Borun LLP (57) ABSTRACT

This invention provides devices and methods for mixing and extruding compositions which are medically and non-medically useful. The devices are particularly useful for mixing substances which are relatively inert when alone but become reactive when mixed. A common feature of all of the devices is that they allow the user to mix and ultimately extrude a composition from a single device which includes a single container or multiple interconnected containers.

14 Claims, 6 Drawing Sheets

U.S. PATENT DOCUMENTS

| | | |
|---|---|---|
| 4,576,152 A | 3/1986 | Muller et al. |
| 4,578,067 A | 3/1986 | Cruz, Jr. |
| 4,587,018 A | 5/1986 | Blombeck et al. |
| 4,600,533 A | 7/1986 | Chu |
| 4,600,574 A | 7/1986 | Lindner et al. |
| 4,606,337 A | 8/1986 | Zimmermann et al. |
| 4,621,631 A | 11/1986 | Paques et al. |
| 4,631,055 A | 12/1986 | Redl et al. |
| 4,640,778 A | 2/1987 | Blomback et al. |
| 4,655,980 A | 4/1987 | Chu |
| 4,675,361 A | 6/1987 | Ward, Jr. |
| 4,683,142 A | 7/1987 | Zimmermann et al. |
| 4,689,399 A | 8/1987 | Chu |
| 4,690,684 A | 9/1987 | McGreevy et al. |
| 4,704,131 A | 11/1987 | Noishiki et al. |
| 4,720,512 A | 1/1988 | Hu et al. |
| 4,725,671 A | 2/1988 | Chu et al. |
| 4,743,229 A | 5/1988 | Chu |
| 4,751,921 A | 6/1988 | Park |
| 4,760,131 A | 7/1988 | Sundsmo et al. |
| 4,786,556 A | 11/1988 | Hu et al. |
| 4,833,200 A | 5/1989 | Noishiki et al. |
| 4,837,285 A | 6/1989 | Berg et al. |
| 4,872,867 A | 10/1989 | Joh |
| 4,874,368 A | 10/1989 | Miller et al. |
| 4,882,148 A | 11/1989 | Pinchuk |
| 4,909,251 A | 3/1990 | Seelich |
| 4,911,926 A | 3/1990 | Henry et al. |
| 4,932,942 A | 6/1990 | Maslanka |
| 4,948,540 A | 8/1990 | Nigam |
| 4,966,601 A | 10/1990 | Draenert |
| 4,978,336 A | 12/1990 | Capozzi et al. |
| 5,019,393 A | 5/1991 | Ito et al. |
| 5,049,393 A | 9/1991 | Noon et al. |
| 5,053,048 A | 10/1991 | Pinchuk |
| 5,071,644 A | 12/1991 | Viegas et al. |
| 5,080,893 A | 1/1992 | Goldberg et al. |
| 5,112,615 A | 5/1992 | Ito et al. |
| 5,116,315 A | 5/1992 | Capozzi et al. |
| 5,126,140 A | 6/1992 | Ito et al. |
| 5,140,016 A | 8/1992 | Goldberg et al. |
| 5,153,003 A | 10/1992 | Kurihara et al. |
| 5,156,613 A | 10/1992 | Sawyer |
| 5,167,960 A | 12/1992 | Ito et al. |
| 5,181,918 A | 1/1993 | Brandhorst et al. |
| 5,182,317 A | 1/1993 | Winters et al. |
| 5,201,745 A | 4/1993 | Tayot et al. |
| 5,209,776 A | 5/1993 | Bass et al. |
| 5,213,580 A | 5/1993 | Slepian et al. |
| 5,223,420 A | 6/1993 | Rabaud et al. |
| 5,244,799 A | 9/1993 | Anderson |
| 5,260,420 A | 11/1993 | Burnouf-Radosevich et al. |
| 5,278,200 A | 1/1994 | Coury et al. |
| 5,292,362 A | 3/1994 | Bass et al. |
| 5,318,524 A | 6/1994 | Morse et al. |
| 5,324,647 A | 6/1994 | Rubens et al. |
| 5,364,622 A | 11/1994 | Franz et al. |
| 5,368,563 A | 11/1994 | Lonneman et al. |
| 5,376,376 A | 12/1994 | Li |
| 5,376,692 A | 12/1994 | Park et al. |
| 5,395,923 A | 3/1995 | Bui-Khac et al. |
| 5,412,076 A | 5/1995 | Gagnieu |
| 5,418,222 A | 5/1995 | Song et al. |
| 5,429,603 A | 7/1995 | Morris |
| 5,447,724 A | 9/1995 | Helmus et al. |
| 5,455,040 A | 10/1995 | Marchant |
| 5,464,396 A | 11/1995 | Barta et al. |
| 5,486,357 A | 1/1996 | Narayanan |
| 5,521,280 A | 5/1996 | Reilly et al. |
| 5,522,804 A | 6/1996 | Lynn |
| 5,525,348 A | 6/1996 | Whitbourne et al. |
| 5,541,167 A | 7/1996 | Hsu et al. |
| 5,541,305 A | 7/1996 | Yokota et al. |
| 5,567,806 A | 10/1996 | Abdul-Malak et al. |
| 5,578,073 A | 11/1996 | Haimovich et al. |
| 5,580,923 A | 12/1996 | Yeung et al. |
| 5,582,596 A | 12/1996 | Fukunaga et al. |
| 5,665,067 A | 9/1997 | Linder et al. |
| 5,697,903 A | 12/1997 | Fischer |
| 5,779,668 A | 7/1998 | Grabenkort |
| 5,785,682 A * | 7/1998 | Grabenkort .................. 604/82 |
| 5,788,670 A * | 8/1998 | Reinhard et al. .............. 604/89 |
| 5,788,702 A | 8/1998 | Draenert |
| 5,844,087 A | 12/1998 | Zimmerman et al. |
| 5,910,315 A | 6/1999 | Stevenson et al. |
| 5,989,215 A | 11/1999 | Delmotte et al. |
| 6,007,613 A | 12/1999 | Izoret |
| 6,063,061 A | 5/2000 | Wallace et al. |
| 6,066,325 A | 5/2000 | Wallace et al. |
| 6,074,663 A | 6/2000 | Delmotte |
| 6,086,594 A | 7/2000 | Brown |
| 6,165,489 A | 12/2000 | Berg et al. |
| 6,241,734 B1 | 6/2001 | Scribner et al. |
| 6,331,172 B1 | 12/2001 | Epstein et al. |
| 6,394,982 B1 | 5/2002 | Ehrenfels |
| 6,395,307 B1 | 5/2002 | Banning et al. |
| 6,406,175 B1 | 6/2002 | Marino |
| 6,425,897 B2 | 7/2002 | Overes et al. |
| 6,447,774 B1 | 9/2002 | Metzner et al. |
| 6,461,325 B1 | 10/2002 | Delmotte et al. |
| 6,461,361 B1 | 10/2002 | Epstein |
| 6,471,670 B1 | 10/2002 | Ehrenfels |
| 6,475,183 B1 | 11/2002 | Epstein et al. |
| 6,488,197 B1 | 12/2002 | Whitman |
| 6,488,650 B1 | 12/2002 | Epstein et al. |
| 6,491,201 B1 | 12/2002 | Whitman |
| 6,554,803 B1 | 4/2003 | Ashman |
| 6,558,687 B2 | 5/2003 | Cederholm-Williams et al. |
| 6,566,345 B2 | 5/2003 | Miller et al. |
| 6,575,940 B1 | 6/2003 | Levinson et al. |
| 6,599,515 B1 | 7/2003 | Delmotte |
| 6,613,020 B1 | 9/2003 | Holm et al. |
| 6,613,054 B2 | 9/2003 | Scribner et al. |
| 6,682,347 B2 | 1/2004 | Aoyagi et al. |
| 6,703,038 B1 | 3/2004 | Schaefer et al. |
| 6,780,411 B2 * | 8/2004 | Lewis et al. ............... 424/94.64 |
| 6,965,014 B1 | 11/2005 | Delmotte et al. |
| 6,972,168 B2 * | 12/2005 | Muir .......................... 435/1.1 |
| 2001/0016749 A1 | 8/2001 | Blatter et al. |
| 2001/0021828 A1 | 9/2001 | Fischer et al. |
| 2001/0034527 A1 | 10/2001 | Scribner et al. |
| 2001/0037091 A1 | 11/2001 | Wironen et al. |
| 2002/0010471 A1 | 1/2002 | Wironen et al. |
| 2002/0087164 A1 | 7/2002 | Speitling |
| 2002/0099385 A1 | 7/2002 | Ralph et al. |
| 2002/0101785 A1 | 8/2002 | Edwards et al. |
| 2002/0119417 A1 | 8/2002 | Ashman |
| 2002/0131933 A1 | 9/2002 | Delmotte |
| 2002/0139088 A1 | 10/2002 | Woodworth et al. |
| 2003/0018339 A1 | 1/2003 | Higueras et al. |
| 2003/0036762 A1 | 2/2003 | Kerr et al. |
| 2003/0040718 A1 | 2/2003 | Kust et al. |
| 2003/0083662 A1 | 5/2003 | Middleton |
| 2003/0219466 A1 | 11/2003 | Kumta et al. |
| 2004/0010260 A1 | 1/2004 | Scribner et al. |
| 2005/0142162 A1 * | 6/2005 | Hunter et al. ............... 424/423 |

FOREIGN PATENT DOCUMENTS

| | | |
|---|---|---|
| DE | 3841397 | 6/1990 |
| EP | 0068149 | 1/1983 |
| EP | 0085166 | 8/1983 |
| EP | 0103290 | 3/1984 |
| EP | 0166263 | 1/1986 |

| | | |
|---|---|---|
| EP | 0187894 | 7/1986 |
| EP | 0213563 | 3/1987 |
| EP | 0262890 | 4/1988 |
| EP | 0369764 | 5/1990 |
| EP | 0372969 | 6/1990 |
| EP | 0 397 589 A1 | 11/1990 |
| EP | 0 470 393 B1 | 2/1992 |
| EP | 0 397 589 B1 | 2/1994 |
| EP | 0611571 | 8/1994 |
| EP | 0747114 A1 | 12/1996 |
| EP | 1118313 A1 | 7/2001 |
| EP | 03 75 9741 | 12/2007 |
| FR | 2448900 | 9/1980 |
| WO | WO87/05491 | 9/1987 |
| WO | WO8902445 | 3/1989 |
| WO | WO9101711 | 2/1991 |
| WO | WO9119519 | 12/1991 |
| WO | WO9215341 | 9/1992 |
| WO | WO9222312 | 12/1992 |
| WO | WO9319805 | 10/1993 |
| WO | WO9321971 | 11/1993 |
| WO | WO9402182 | 2/1994 |
| WO | WO9422503 | 10/1994 |
| WO | WO9617638 | 6/1996 |
| WO | WO9622115 | 7/1996 |
| WO | WO9639212 | 12/1996 |
| WO | WO9802098 | 1/1998 |
| WO | WO9967015 | 12/1999 |
| WO | 02/068010 A1 | 9/2002 |

OTHER PUBLICATIONS

Bailey, et al., "Fibrin Films in Neurosurgery . . . ," Chemical, Clinical, and Immunological Studies on the Products of Human Plasma Fractionation, Harvard Medical School, Paper No. 27, 597-600 (Feb. 17, 1994).
Brands, et al., "Die Anwendung Des Fibrinklebers zur Prophylaxe und Terapie intraabdomineller Adhasionen," Der Chirug, 61, 22-26, (1990).
Chmielewski et al., "Fibrin Gel Limits Intra-Abdominal Adhesions Formation," The American Surgeon, 58 (9), 590-593 (Sep. 1992).
Connoly et al., "The Prevention and Treatment of Intestinal Adhesions," International Abstracts of Surgery, 110 (5), 417-431 (May 1960).
Copley et al., "The Binding of Human Fibrinogen To Native and Fraction Fibrins and The Inhibition of Polymerization of New Human Fibrin Monomer by Fibrinogen," Life Sciences, 3(11) 1293-1305 (1964).
Cronkite et al , "Use of Thrombin and Fibrinogen in Skin Grafting," J.A.M.A., 124(14), 976-968 (Apr. 1, 1994).
De laco et al., "Fibrin Sealant in Laparoscopic Adhesion Prevention in the Rabbit Uterine Horn Model," Fertility and Sterility, 62(2), 400-494, (Aug. 1994).
Feldman et al., "Tissue Adhesives in Wound Healing," University of Alabama at Birmingham, 1-38 (May 1994).
Ferry, "The conversion of Fibrinogen to Fibrin: Events and Recollections from 1942 to 1982," Annals of the New York Academy of Sciences, Molecular Biology of Fibrinogen and Fibrin, New York Academy of Science, 408, 1-5 (1983).
Ferry et al., "Fibrin Clots, Fibrin Films, and Fibrinogen Plastics," Chemical, Clinical, and Immunological Studies on the Products of Human Plasma Fractionation, Harvard Medical School, Paper No. 22, 566-572 (Feb. 17, 1994).
Ferry et al., "Preparation and Properties of Serum and Plasma Proteins. IX. Human Fibrin in the Form of an Elastic Film," Harvard Medical School, Paper No. 48, 69, 400-409 (Feb. 1947).
Fujita et al., "Prevention of Surgical Adhesions Using Aerosoled Biodegradable Polyesters," The 20$^{th}$ Annual Meeting of the Society for Biomaterials, Apr. 5-9, 1994.
Gabbay, "The Need for Intensive Study of Pericardial Substitution After Open Heart Surgery," Trans. Am. Soc. Artif. Intern. Organs, vol. XXXVI, 789-791 (1990).

Gauwerky et al., "The Effect of Fibrin Glue and Peritoneal Grafts in the Prevention of Intraperitoneal Adhesions," Archives of Gynecology and Obstetrics, 247, 161-16 (1990).
Giovanettoni, "The Tisseel Method, History Background, Application, Techniques and Indications of Fibrin Sealing in Modern Surgery," Immuno., 1-70 (Jan. 1985).
Grey, "Fibrin as a Haemostatic in Cerebral Surgery," Surgery, Gynecology and Obstetrics, 21, 452-454 (1915).
Haney et al., "Exapnded-Polytetrafluoroethylene But Not Oxidized Regenerated Cellulose Prevents Adhesion Formation and Reformation in a Mouse Uterine Horn Model of Surgical Injury," Fertility and Sterility, 60 (3), 550-558 (Sep. 1993).
Harvey, "The Use of Fibrin Paper and Forms in Surgery," Boston Medical and Surgical Journal, vol. CLXXIV (1s), 658-659 (May 4, 1916).
Hill-West et al., "Prevention of Postoperative Adhesions in the Rat by in Situ Photopolymerization of Bioresorbable Hydrogel Barriers," Obstetrics and Gynecology, 83 (1), 59-64 (Jan. 1994).
Horn et al., "Treatment of Stress Incontinence by a Fibrin Bioplast," British Journal of Obstetrics and Gynecology, 82, 61-63 (Jan. 1975).
Joyce et al., "Alteration in Pericardial Adhesion Formation Following Pretreatment with Fibrin Glue," Journal of Applied Biomaterials, 2, 269-271 (1991).
Lindenberg et al., "Studies on Prevention of Intra-Abdominal Adhesion Formation by Fibrin Sealant," Acta Chir Scand, 151, 525-527 (1985).
Linsky et al., "Adhesion Reduction in the Rabbit Uterine Horn Model Using an Absorbable Barrier, TC-7," The Journal of Reproductive Medicine, 32 (1), 17-20. (Jan. 1987).
Maddox et al., "An Evaluation of the Bionite Hydrophilic Contact Lens for Use in a Drug Delivery System," Annals of Opthamology, 789-790, 793-794, 796, 798, and 802 (Sep. 1972).
Marchac et al., "The Use of Sprayed Firbrin Glue for Face Lifts," European Journal of Plastic Surgery, 10, 139-143 (1987).
Matsuda et al., "Photoinduced Prevention of Tissue Adhesion," ASAIO Journal, M154-M157 (1992).
Miyazaki et al., "Use of Fibrin as a Carrier for Drug Delivery: A Long-Acting Delivery System for Pilocarpine Into the Eye," Chem. Pharm. Bull., 30 (9), 3405-3407 (1982).
Montz et al., "Effectiveness of Two Barrires at Inhibiting Post-Radical Pelvic Surgery Adhesion," Gynecologic Oncology, 48, 247-251 (1993).
Oka et al., "Effect of a Biologic Glue on the Leakage Rate of Experimental Rectal Anastomoses," The American Journal of Surgery, 143, 561-564 (May 1982).
Sasaki et al., "Stable Complex of Fibrinogen and Fibrin," Science, 152, 1069 and 1071-1072 (May 20, 1966).
Sawhney et al., "Bioerodible Hydrogels Based on Photopolymerized Poly (ethylene Glycol)-co-ploy (a-hydroxy acid) Diacrylate Macromers," Macromolucles, 26 (4), 581-587 (1993).
Schlag et al , "In Vitro Properties of Mixtures of Fibrin Seal and Antibiotics," Biomaterials, 4, 29-32 (Jan. 1983).
Schier et al., "Dura Covered With Firbrin Glue Reduces Adhesions in Abdominal Wall Defects," Eur. J. Pediatr. Surg., 1, 343-345 (1991).
Sheppard et al., "Inhibition of Intra-Abdominal Adhesions: Fibrin Glue in a Long Term Model," The American Surgeon, 59 (12), 786-790 (Dec. 1993).
Shimanuke et al., "Localized Prevention of Postsurgical Adhesion Formation and Reformation with Oxidized Regenerated Cellulose," Journal of Biomedical Materials Research, 21, 173-185 (1987).
Sierra, "Flbrin Sealant Adhesive Systems: A Review of Their Chemistry, Material Properties and Clinical Applications," Journal of Biomaterials Applications, 7, 309-352 (Apr. 1993).
The Surgical Membrane Study Group, Prophylaxis of Pelvic Sidewall Adhesions with Gore-Tex Surgical Membrane: A Multicenter Clinical Investigation, Fertility and Sterility, 57 (4), 921-923, (Apr. 1992).
Thompson et al., "Reduced Human Peritoneal Plasmiogen Activating Activity: Possible Mechanism of Adhesive Formation," Br. J. Surg., 76 (4), 382-384 (Apr. 1989).

Tulandi, "Effects of Fibrin Sealant on Tubal Anastomosis and Adhesion Formation," Fertility and Sterility, 56 (1) 136-138 (Jul. 1991).

Urry et al., "Properties and Prevention of Adhesions Applications of Bioelastic Materials," Mat. Res. Soc. Symp. Proc., 292 (1993).

deVirgilio et al., "Fibrin Glue Inhibits Intra-Abdominal Adhesion Formation," Arch. Surg., 125, 1378-1382 (Oct. 1990).

Bohner et al., "Theoretical Considerations on the Injectability of Calcium Phosphate Cements", Poster Presentation P124, 17$^{th}$ European Society for Biomaterials Conference, 1 page (2002).

Almirall et al., "Effect of Storage Temperature on Injectability and Setting Time of some Calcium Phosphate Cements", Proceedings of the 17th European Conference on Biomaterials, reference T70, 1 page (Barcelona, 2002).

Baroud et al., "Rheological Characterization of Concentrated Aqueous β-tricalcium Phosphate Suspensions: The Effect of Liquid-to-Powder Ratio, Milling Time, and Additives", *Acta Biomaterialia*, 1:357-63 (2005).

Bohner et al., "Injectability of Calcium Phosphate Pastes", *Biomaterials*, 26:1553-63 (2005).

Chow et al., "A Natural Bone Cement—Laboratory Novelty Led to the Development of Revolutionary New Biomaterials", *J. Res. Natl. Inst. Stand. Technol.*, 106:1029-33 (2001).

Habib et al., "Mechanisms Underlying the Limited Injectability of Hydraulic Calcium Phosphate Paste", *Acta Biomaterialia*, 4:1465-71 (2008).

Habib et al., "Mechanisms Underlying the Limited Injectability of Hydraulic Calcium Phosphate Paste. Part II: Particle Separation Study", *Acta Biomaterialia*, 6:250-6 (2010).

Hartgerink et al., "Self-Assembly and Mineralization of Peptide-Amphiphile Nanofibers", *Science*, 294:1684-8 (Nov. 23, 2001).

Blomback et al., "Fibrin Gels and Their Possible Implication for Surface Hemoheology in Health and Disease," Annals New York Academy of Sciences, 397-409 (1983).

Sawhney et al., "Optimization of Photopolymerized Bioerodible Hydrogel Properties for Adhesion Prevention," Journal of Biomedical Materials Research, 28, 831-838 (1994).

Tarlov et al., "Plasma Clot Suture of Nerves," Archives of Surgery 44-58 (1943).

* cited by examiner

DEVICES FOR MIXING AND EXTRUDING MEDICALLY USEFUL COMPOSITIONS

This application is a continuation application of U.S. application Ser. No. 10/265,076, filed Oct. 4, 2002 now U.S. Pat. No. 7,135,027, which is hereby incorporated by reference herein.

CROSS-REFERENCES TO RELATED APPLICATIONS

Not applicable.

FEDERALLY SPONSORED RESEARCH OR DEVELOPMENT

Not Applicable.

BACKGROUND OF THE INVENTION

1. Technical Field

This invention relates to medical devices for mixing and extruding medically useful compositions, such as those used as bone replacement materials.

2. Background of the Invention

Certain medically useful substances are composed of component parts that require mixing prior to use. One such example is the mixing of the components used in preparing compositions as replacement materials for bones. Bone replacement materials typically are composed of a mineral component and a glue that surrounds and binds the mineral component. Often the mineral component is a calcium based mineral, and the glue component is a fibrin glue. The fibrin glue is formed by mixing fibrinogen and thrombin components.

Bone replacement material is typically mixed using a mortar and pestle and then applied as a paste. The mortar and pestle method, however, often destroys or greatly compromises the integrity of the fibrin glue matrix. This is due to the mechanical grinding action associated with using the mortar and pestle. Other similar methods involve mixing of the components on a flat surface using a spatula or like implements. In this regard, another disadvantage of current methods of mixing bone replacement materials is that they do not provide for final mixtures wherein the component parts are distributed homogeneously and in precise quantities.

There is therefore a need for medical devices that facilitate the mixing of substances that, when mixed, yield medically useful compositions. More specifically, there is a need for such devices that can conveniently and efficiently mix the component parts of bone replacement materials. Ideally the devices should be of a nature such that the mixing of the component parts, as well as the ultimate extrusion of the final composition, can be carried out wholly within the devices themselves.

SUMMARY OF THE INVENTION

The present invention provides devices and methods for mixing and extruding compositions which are medically and non-medically useful. The device is particularly useful for mixing substances which are relatively inert when alone but become reactive when mixed. A common feature of all of the devices is that they allow the user to mix and ultimately extrude a composition from a single device which includes a single container or multiple interconnected containers.

The device comprises a chamber which contains a mineral component and a glue component. The device further provides a member associated with the chamber for delivering a reaction product of the mineral and the glue.

In another embodiment, the device has a first container having a first opening which is adapted to contain a first chemically reactive substance. The device further includes a second container having a second opening which is adapted to contain a second chemically reactive substance and a third container have a third opening. A connector that connects the first opening, second opening, and third opening is provided such that the first chemically reactive substance and the second chemically reactive substance can travel through the connector and through the third opening into the third container to form a composition. A member is provided for extruding the composition from the third container.

In another embodiment, the device includes a first container having a first opening which is adapted to contain a first chemically reactive substance. The device further includes a second container having a second opening which is adapted to contain a second chemically reactive substance. A connector is provided that connects the first opening and second openings such that the first chemically reactive substance can travel through the connector and through the second opening into the second container wherein the first and second chemically reactive substances can react to form a composition. The device further includes means for extruding the composition from the second container.

According to a further aspect of the invention, the device includes a syringe. The syringe has a hollow cylindrical tube with a forward opening, and a rear opening through which a piston is fitted. The forward opening is fitted such that a removable cap can cover the forward opening. The removable cap contains a removable cover that covers a port into which a luer tip can be inserted.

The present invention further provides a method for mixing and extruding a bone replacement material. The method comprises the steps of providing a device comprising at least one container wherein at least two components of the bone replacement material are mixed and extruded after mixing; placing the components of the bone replacement material into the device; mixing the components to form the bone replacement material; and extruding the bone replacement materials from the device.

In still another embodiment, the method comprises the steps of providing a syringe having a hollow cylindrical tube with a forward opening, and a rear opening through which a piston is fitted; the forward opening being fitted such that a removable cap can cover the forward opening; and the removable cap containing a removable cover that covers a port into which a luer tip can be inserted; placing at least two chemically reactive substances in the tube; causing the substances to react to form a composition; and extruding the composition from the tube.

In yet another embodiment the method comprises the steps of providing a syringe having a hollow cylindrical tube with a forward opening, and a rear opening through which a piston is fitted; the forward opening being fitted such that a removable cap can cover the forward opening; and the removable cap containing a removable cover that covers a port into which a luer tip can be inserted; placing a first reactive substance in the tube and freezing the first reactive substance; placing a second non-reactive substance on top of the first reactive substance and freezing the tube again, placing a second reactive substance on top of the non-reactive substance and freezing the tube, sublimating the non-reactive substance during the freezing process leaving a void between the first and second reactive substances, aspirating water in the tube causing the first and second substance to react to form a composition; and extruding the composition from the tube.

According to a further aspect of the invention, the method comprises the steps of providing a syringe having a hollow cylindrical tube with a forward opening, and a rear opening through which a piston is fitted; the forward opening being fitted such that a removable cap can cover the forward opening; and the removable cap containing a removable cover that covers a port into which a luer tip can be inserted, placing a first reactive component into the syringe, placing a second reactive component into the syringe; and mixing the first and second components together, whereby the first and second reactive components mix to form a composition without any change in total volume.

These and other aspects and attributes of the present invention will be discussed with reference to the following drawings and accompanying specification.

DETAILED DESCRIPTION OF THE INVENTION

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

This invention provides medical devices for mixing and delivering compositions that are medically useful. The invention also provides methods for mixing and delivering such compositions. In addition, the devices and methods of the present invention may also be used for non-medical compositions where a solid porous substance has to be mixed with at least one liquid.

It is contemplated that the devices of the present invention will be used for the purpose of mixing substances that are relatively inert when alone but become reactive when mixed. When mixed, the substances can form a desired composition that is medically or non-medically useful. A common thread among the devices of the present invention is that they allow the practitioner to mix and ultimately extrude the desired composition from a single device that comprises a single container or multiple interconnected containers. In general the device can be used for mixing macroporous biphasic calcium phosphate (MBCP) or any calcium based mineral with fibrin or non fibrin glues. In addition, the devices can be used for mixing MBCP or a calcium based mineral with biological fluids or a liquid such as water, buffer, jelling agent, corn starch, or the like. It is also possible to use the devices of the present invention to mix MBCP or a calcium based mineral with a polymer or copolymer such as polyethylene, polypropylene, PLA, PGA, polyvinyl alcohol, polymethyl methacrylate, or silicone. It is further possible to use the present invention to mix a non-calcium based mineral such as $SiO_2$ based glasses or glass ceramic with fibrin luers, non-fibrin glues, biological fluid including cells or a liquid as described above.

While the devices of the present invention can be used to mix virtually any substances that yield a useful product, the inventor contemplates that such devices are especially beneficial for mixing and delivering compositions that are used for the replacement, repair and augmentation of mammalian bone structures.

Hydroxyapatite (HA) or biphasic materials such as MBCP are currently used as a biomaterial implant in orthopedic surgeries for replacing or supplementing bone. MBCP is a biocompatible substance that has defined mechanical and osteoconductive properties as well as the capability to bond adjacent hard and soft tissues.

A major problem in the reconstruction of a bone defect with hydroxyapatite granules is the instability, dislocation and migration of the granules from the cavity. To eliminate this type of problem, orthopedic surgeons often mix the MBCP granules with a two-component fibrin glue. The main advantage is the application of the implant as a moldable paste that prevents dislocation of the granules, maintaining the required bulk and shape during the tissue ingrowth.

The common components of bone repair material are often therefore a granular mineral component that is surrounded by a glue component. The glue component is typically a mixture of at least two chemically reactive components. For example, commercially available fibrin glues include BERIPLAST® from Aventis Behring, BIOCOL® from LFB, BOHELAL® from Kaketsuken, QUIXIL™ from Omrix, HEMASEEL® from Hemacure. In addition to the above, home made glues are known from automated systems such as VIVOSTAT™, CRYOSEAL®, AUTOSEAL™ and BIOCORAL®, as well as synthetic cyanoacrylate based glues such as DERMABOND®, LIQUIDERM™, SOOTHE-N-SEAL™, all available from Closure, INDERMIL™ from Locite, LIQUID-BAND® from MedLogic, and GLUBRAN® from GEM. Other commercially available products include non-fibrin glues and non-synthetic products such as FLOSEAL® from Fusion Medical Technologies, COSEAL™ from Cohesion, FOCALSEAL® from Focal, as well as plasma derivative sealants such as FIBRX™ from Cryolife, and non-sintered hydroxyapatite with crystalline nanoparticulate such as OSTIM™. Provided below is a more detailed description of the typical component parts of bone repair materials.

I. Components for Fabricating Bone Repair/Replacement Materials

Fibrin glues can be used as bonding agents to adhere to and around the mineral component of a bone replacement material. Fibrin sealants/glues are well-known in the art for use in haemostasis, tissue sealing and wound healing and have been commercially available for more than a decade. Fibrin glues irritate the last step of the blood coagulation cascade and are usually commercialized as kits comprising two main components. The first component is a solution comprising fibrinogen and factor XIII, while the second component is a thrombin-calcium solution. After mixing of components, the fibrinogen is proteolytically cleaved by thrombin and thus converted into fibrin monomers. In the presence of calcium, Factor XIII is also cleaved by thrombin into its activated form (FXIIIa). FXIIIa cross-links the fibrin monomers to a three-dimensional network commonly called "Fibrin Matrix."

The components of the fibrinogen and thrombin can be prepared from plasma by conventional precipitation and purification steps. When the patient to be treated is a human being, human plasma will be preferred. The source of the plasma may be either pooled donor blood or single donor blood obtainable from blood centers, respectively. Care should be taken that state of the art controls are performed to detect viral contamination. During the process of manufacturing, the products may be sterilized by standard techniques as well. In order to avoid any risk of contamination, the components could be prepared from pre-operative autologous blood donation. It will be understood that the components of the first or the second solution or their functional analogues may also be prepared by using the methods of molecular genetics.

Conveniently, in the light of the present disclosure, commercially available two-component fibrin glue kits may be used for the preparation of the fibrin film of the present invention. The required constituents are usually contained in the kits in the form of lyophilized concentrates and have to be reconstituted as per the technical data sheet provided with the respective kit. The desired thrombin concentration is prepared by diluting an aliquot of the reconstituted thrombin solution with sterile calcium chloride solution, preferably 20 mM or 40 mM calcium chloride or the appropriate buffer that maintains the ionic strength of the solution.

The inventors propose that the fibrin glue used in connection with the present invention may also be obtained from one vial containing all the required components. In this case, the catalytic agents for the fibrinogen-fibrin conversion and the cross-linking of soluble fibrin, respectively, are inactivated and the polymerization is only started by induction through a change in pH, ionic strength, exposure to light or the like after the content of said vial had been applied to a solid support. By way of example, photo-sensitive inhibitors of thrombin and thrombin-like molecules could be used for this purpose. The fibrin glue of the invention may also be prepared in accordance with Copley and Luchini, (Life Sciences 3, 1293-1305, 1964) and Sasaki et al. (Science 152, 1069-1071, 1966) by starting from soluble fibrinogen-fibrin monomer complexes precipitated in the cold, redissolved at high temperature and which are then cross-linked with factor XIII and calcium.

In addition, jelling agents such as hydroxypropylmethylcellulose, carboxylmethylcellulose, chitosan may be used to improve washout resistance before hardening of the cement occurs as described in the J. Res. Natl. Inst. Stand. Technol. 106, 1029-1033 (2001). The bone replacement material can also include the addition of self assembling amphiphile peptides designed to mimic aggregated collagen fibers (extracellular matrices) and also form supramolecular networks. A subset of this family can also be engineered to nucleate hydroxyapatite nanocrystals to serve as artificial extracellular matrice for bone regeneration as disclosed in J. D. Hartgerink, E. Beniash, and S. I. Stupp: Self-Assembly and Mineralization of Peptide-Amphiphile Nanofibers, *Science,* 294, (5527) 1684 (2001).

In accordance with the invention, a fibrinogen solution preferably contains fibrinogen and factor XIII (10-40 IU/mL). The concentration of fibrinogen is expressed as the total protein concentration (preferably from about 15-140 mg/mL and more preferably 30-110 mg/mL) and the percentage of clottable protein contained therein. It is also preferred that the fibrinogen solution have a viscosity that allows the solution to be manipulated using pressures generated using a hand-operated syringe. The fibrinogen solution should have a viscosity of less than 300 centipoise, more preferably less than 100 centipoise, and most preferably from 5-50 centipoise or any combination or subcombination of ranges therein.

The inventors prefer the percentage of clottable protein to be at least 80% and preferably equal to or greater than 90%. Of course, those of skill in the art will recognize that a variety of other constituents may be included in the fibrinogen solution, for example albumin, plasminogen and tensides. The thrombin solution preferably has a concentration from about 0.01 IU/mL to about 10,000 IU/mL, even more preferably from about 200 to about 500 IU/mL, and most preferably from about 400 to about 500 IU/mL or any combination or subcombination of ranges therein (depending on the desired biophysical parameters of the material to be obtained) and calcium in a concentration of up to 45 mM. For simplification, the thrombin concentration normally given in IU/mL, will in the following frequently be indicated in IU.

So-called fibrin "hydrogels" are know in the art and can be mixed using the devices and methods of the present invention. Examples of such hydrogels include those prepared in accordance with U.S. patent application Ser. No. 09/566,019, which is hereby incorporated by reference. In addition to the above, cross-linked hydrogels and bioadhesives, such as those described in U.S. Pat. Nos. 6,066,325; 6,063,061; and 6,007,613, all of which are incorporated herein by reference, can also be used with the devices and methods of the present invention.

Other chemically reactive substances can be used as the glue-like component to bind to and around the mineral component of the bone replacement substance. Such other substances can include, for example, sodium alginate and calcium chloride, collagen and a cross-linking agent such as low pH buffer, chitin, formaldehyde, glutaraldehyde, dialdehyde starch, hexamethylene diisocyanate and certain polyepoxy compounds. Examples of suitable cross-linking agents are disclosed in U.S. Pat. No. 6,165,489. Collagen compositions can be prepared in accordance with U.S. Pat. No. 4,061,787, which relates to formable collagen compositions including cross-linking agents and U.S. Pat. No. 5,643,464, which relates to collagen with a sterile, dry cross-linking agent. Alginate compositions include those described in U.S. Pat. No. 6,395,307, which discloses a cross-linking agent of aluminum or calcium solutions.

The common feature among these and other glue materials used in the present invention is that the material does not become glue until the individual components are mixed together. By mixing the components, a chemical reaction occurs whereby the glue composition forms.

Depending on the preferences of the practitioner of the present invention, the glue component can additionally include components such as, for example, hardeners, cross-linking agents, pigments, processing aids (such as lubricant, plastifying agent, surfactant, viscosity reducing agent, etc.), fibers, polymers, copolymers, antibody, antimicrobial agent, agent for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting or stimulating the growth and/or attachment of endothelial cells on the cross-linked fibrin, growth factors, growth factors for heparin bond, substances against cholesterol, pain killers, collagen, osteoblasts, drugs, etc. and mixtures thereof.

Drugs which may be used in accordance with the present invention include, but are not limited to, antimicrobial compositions, including antibiotics, such as tetracycline, ciprofloxacin, and the like; antimycogenic compositions; antivirals, such as gangcyclovir, zidovudine, amantidine, vidarabine, ribaravin, trifluridine, acyclovir, dideoxyuridine, and the like, as well as antibodies to viral components or gene products; antifungals, such as diflucan, ketaconizole, nystatin, and the like; and antiparasitic agents, such as pentamidine, and the like. The drugs may further include anti-inflammatory agents, such as .alpha.- or .beta- or .gamma.-interferon, alpha.- or beta.-tumor necrosis factor, and the like, and interleukins.

As noted above, pursuant to the devices and methods of the present invention, the glue component can be mixed with a mineral component to form a bone replacement composition. The mineral component of bone replacement material preferably contains calcium. Others, however, can include, for example, calcium carbonate, calcium sulfate, calcium sulfonate, polycalicum phosphate and mixtures thereof. Commercially available systems useful with the devices and methods of the present invention include Norian SRS® from Norian Corporation, PRO-OSTEON™ from Interpore Cross, FRIOS ALGIPORE® and VITOSS® from Orthovita, BIO-SORB CERASORB® from Curasan, BIOBON® from Etex Corporation, and TRIOSITE® and COLLAGRAFT™ from Zimmer. When used with the devices and methods of the present invention, the composite fulfills the general equation $Volume_{Mineral} = Volume_{Mineral} + Volume_{Glue}$.

Calcium based mineral preparations are typically available in granular form with various sized granules with varying levels of porosity. A common commercially available preparation is a macroporous biphasic calcium phosphate (MBCP), which can consist of a combination of HA and beta-tricalcium phosphate. A suitable MBCP product is available from Biomatlante (Fr).

A common MBCP material can contain a blend of approximately 60% HA and 40% beta-tricalcium phosphate. Such granules are typically described in terms of an apparent and skeletal density. This means, for example, that 1.0 g of MBCP granules from Biomatlante, occupies a volume of 1.8 mL (i.e., its skeletal density). This is explained by the open porosity of the material which has been measured to be approximately 80.5%. In other words, approximately 1.45 mL of the 1.8 mL volume of MBCP is occupied by air depending on the skeletal density of the material used.

The porosity of MBCP makes it an ideal material for bone replacement applications because glues such a fibrin glue can enter the pores of the MBCP which facilitates strong bonding. Moreover, MBCP can be produced with other shapes, sizes and porosity leading therefore to different skeletal porosities which can be predicted, necessitating different fibrin glue volume. More specifically, mixing is based on the replacement of the volume of air contained in the pores of the MBCP material by an equal volume of fibrin glue when these components are mixed in a container. Therefore, when mixed in a container in which a defined initial MBCP volume can be determined, the final volume of the MBCP/glue mixture typically will be the same as the initial volume of the MBCP. This concept is represented by the formula: $V_{MBCP} = V_{MBCP} + V_{Glue}$. This not only applies to MBCP, but will apply to any calcium based mineral used to obtain a composite such that the volume of liquid necessary will fulfill the equation $V_{mineral} = V_{mineral} + V_{Glue}$. Depending on the characteristics of the calcium based mineral such as the porosity, size, and shape, the volume of the liquid can be different.

Pursuant to the present invention, MBCP can be combined with a glue by an alternative means. For example, MBCP granules can initially be coated with thrombin. When the practitioner desires to form the bone replacement material, fibrinogen can be introduced to the thrombin-coated MBCP granules. Pursuant to the chemical reactions discussed previously, the thrombin and fibrinogen will react to form a fibrin glue that surrounds the MBCP granules. One reason for using thrombin-coated MBCP is to achieve a comparatively slow reaction between the thrombin and fibrinogen. Moreover, the catalyst is adsorbed on the solid surface which simplifies the device. Once the substrate is injected into the micro, macro, and inter granular spaces, it reacts with the adsorbed thrombin almost at the same time leading to the formation of a homogeneous and regular fibrin network formed by thick twisted fibers. In this sense, this is heterogeneous catalysis since the reagents combine and transform at the interface between the liquid and the surface of the catalyst, as opposed to homogeneous catalysis in which the catalyst is dissolved in a liquid.

Coating with thrombin can be achieved by washing MBCP granules with a thrombin solution. Preferably, the thrombin solution will include thrombin (10 IU/mL) and $CaCl_2$ (2.5 mM up to 40 mM). After washing with the thrombin solution, the MBCP granules are preferably washed with a $CaCl_2$ (2.5 mM) solution. As soon as the MBCP is mixed with a solution of thrombin, thrombin adsorbs on the granules. The unadsorbed thrombin can be removed by washing with a low ionic strength buffer and then freeze dried.

Another method of coating MBCP with thrombin involves using the DUPLOJECT™ system from Baxter Bioscience. The device consists of two syringes which contain thrombin and fibrinogen solution, respectively. The DUPLOJECT is then connected to a syringe containing MBCP granules. The thrombin is then injected into the MBCP containing syringe and then the excess liquid is reaspirated by pulling the plunger of the thrombin syringe back. The fibrinogen is then injected into the syringe containing the thrombin adsorbed MBCP granules.

Still yet another method of coating MBCP with thrombin is to have the thrombin layer lyophilized or frozen (−18° C. to −80° ) on the top or bottom of the MBCP granules in the same syringe. A diluent is then aspirated into the syringe, thus dissolving the thrombin which then adsorbs on the MBCP granules.

II. Delivery Devices

Pursuant to the present invention, devices are provided that facilitate mixing and extrusion or delivery of medically useful compositions. The devices enable mixing and extrusion of components in single devices, thus obviating the need for multiple mixing steps that typically result in mixtures that are messy and contain imprecise blending of the component parts.

Figure 1A:
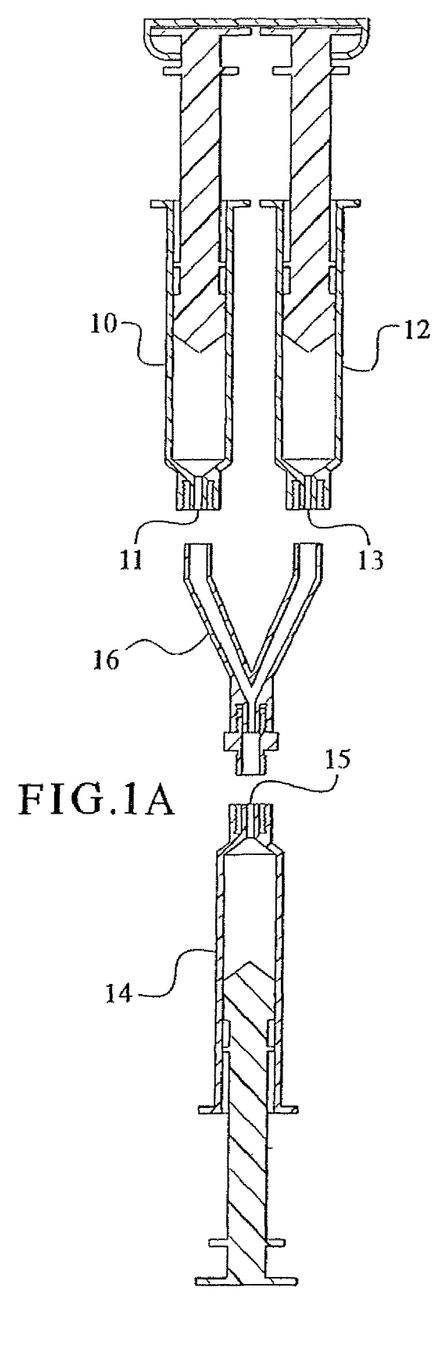
FIG. 1 illustrates a schematic view of a device of the present invention.
Figure 1B:
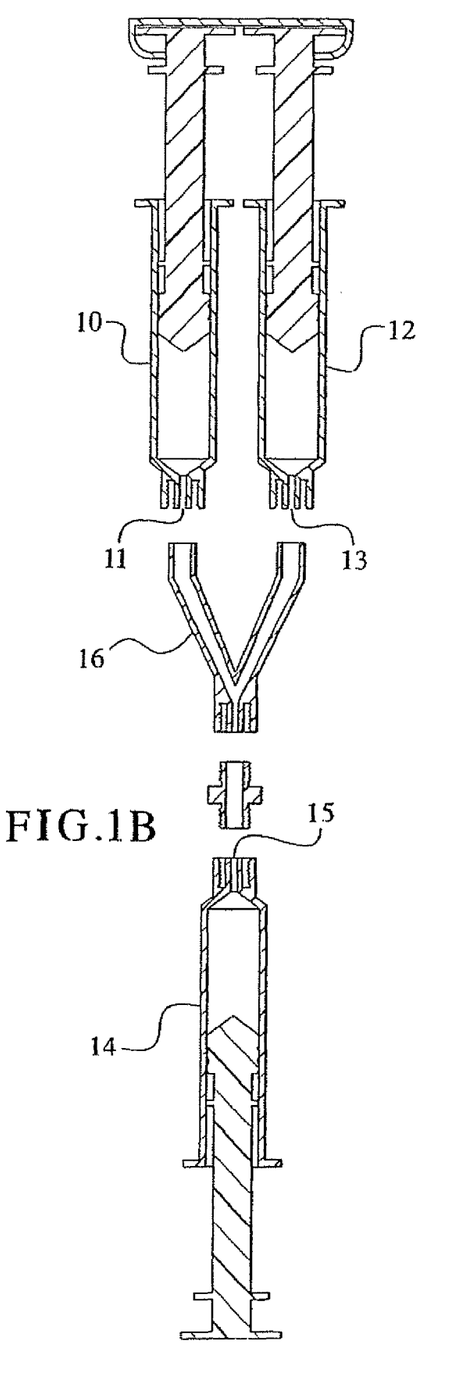

FIG. 1 shows a medical device of the present invention that allows for mixing of chemically reactive substances, and ultimately the extrusion of the final composition resulting from the chemical reaction between or among those substances. The medical device features a first container 10 having a first opening 11, the first container being adapted to contain a chemically reactive substance. A second container 12 is also provided having a second opening 12, the second container being adapted to contain a chemically reactive substance. Additionally, there is a third container 14 having a third opening 15. A connector 16 connects the first opening 11, second opening 13, and third opening 15 such that the chemically reactive substances can travel into the connector to begin the mixing process, and thereafter capable of traveling through the third opening 15 into the third container 14. After a composition is formed and present in the third container, the third container can be disconnected from the connector. The composition can be extruded from the third container after removing or cutting the luer end of the third container.

The containers utilized with the device are preferably syringes, although non-syringe containers can be employed. Syringes are preferred because they are well suited for the controlled delivery of volumetric quantities and because extrusion of contents therefrom can be achieved easily, safely, and reliably by using hand pressure when depressing the syringe plungers. Preferred syringes for use with the present invention include those described in U.S. patent application Ser. No. 09/801,864 entitled "Polymeric Syringe Body and Stopper," which is incorporated herein by reference and made a part hereof. The connector 16 is preferably a Y-shaped female-female leur connection piece that is known in the art for the purpose of connecting multiple syringes. Depending on the particular application, various types of connectors may be used. Moreover, it may be desirable to employ more than one connector.

If the first and second containers are syringes, it is preferred that they constitute a parallel dual syringe assembly whereby the plungers of both syringes can easily be retracted and depressed either simultaneously or sequentially. In this regard, simultaneous extrusion can provide for the transfer of precise quantities of the first and second chemically reactive substances into the connector for mixing. This type of dual syringe system is know in the art and is exemplified by the system provided by Baxter BioScience under the name of DUPLOJECT™ and by Hemaedics, Inc. and sold under the trade name DUOFLO. Similarly, if syringes are used, it is preferred that a Y-shaped connector be used to connect the three syringes.

The third container can additionally contain a substance that can become integrated into the final composition. More specifically, after the substances from the first two containers are transferred through the connector into the third container, those substances will mix with the contents of the third container to form a final composition.

The device can be used to mix and extrude any substances that, when mixed, produce a medically useful composition. In addition, the device can also be used for non-medical applications such as the embedding of resin or mixing without sedimentation. However, when this invention is used for purposes of mixing and extruding bone replacement materials, it is preferred that the first two containers contain the fibrinogen and thrombin components, respectively, that are necessary to form a fibrin glue. In this case, it is additionally preferred that the contents of the third container contain a mineral component such as biphasic calcium phosphate material (MBCP). Of course other types of reactive glue components can be present in the first and second containers, and other types of mineral substrates can be used in the third container.

Figure 2:
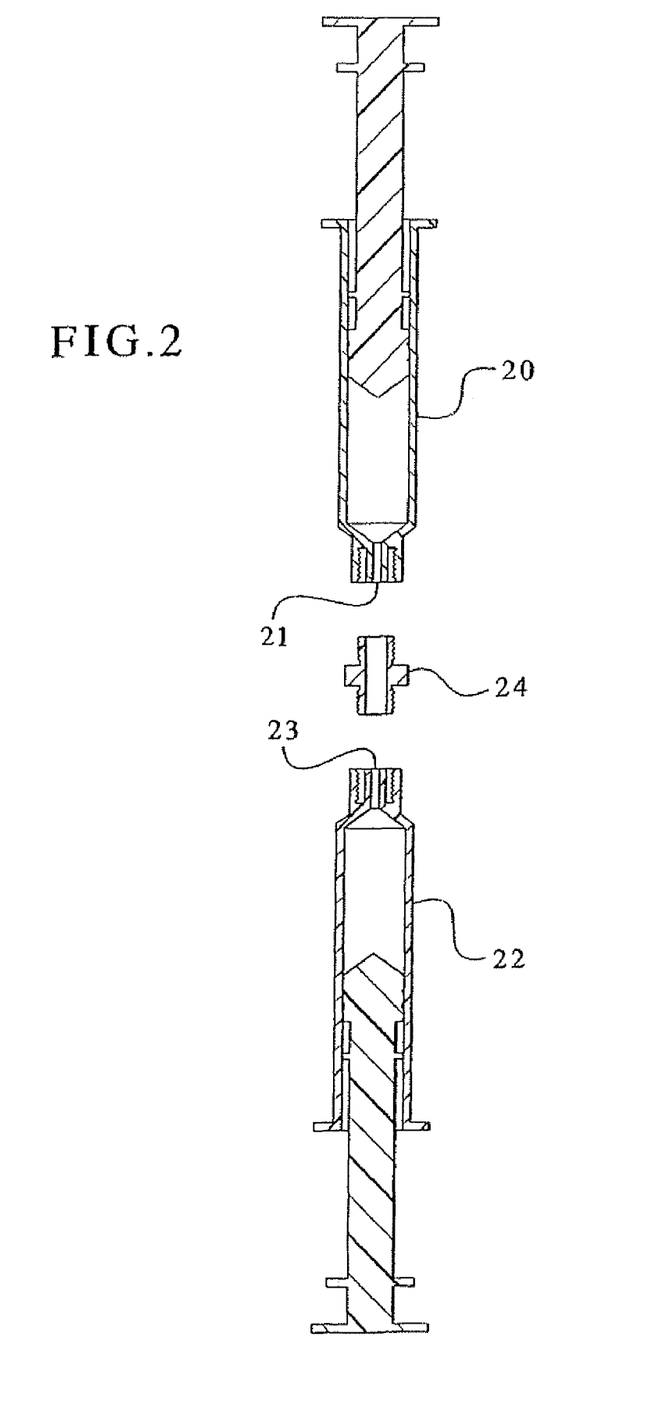
FIG. 2 illustrates a schematic view of another device of the present invention.

FIG. 2 shows another medical device of the present invention that allows for mixing of chemically reactive substances, and ultimately the extrusion of the final composition resulting from the chemical reaction between or among those substances. The medical device features a first container 20 having a first opening 21, the first container being adapted to contain a chemically reactive substance. The device additionally features a second container 22 having a second opening 23, the second container being adapted to contain a chemically reactive substance. A connector 24 connects the first opening and second openings 21, 23 such that the substance from the first container 20 can travel through the connector 24 and through the second opening 23 into the second container 22 where it can react with the substance(s) contained in the second container 22. The composition can be extruded from the second container after removing or cutting the luer end.

The containers utilized with the device are preferably syringes. Syringes are preferred because they are well suited for the controlled delivery of volumetric quantities and because extrusion of contents therefrom can be achieved easily, safely, and reliably by using hand pressure when depressing the syringe plungers.

When syringes are used for the first and second containers 20, 22, the connector 24 is preferably a female-female luer. Depending on the particular application, various types of connectors may be used. Moreover, it may be desirable to employ more than one connector.

Figure 3:
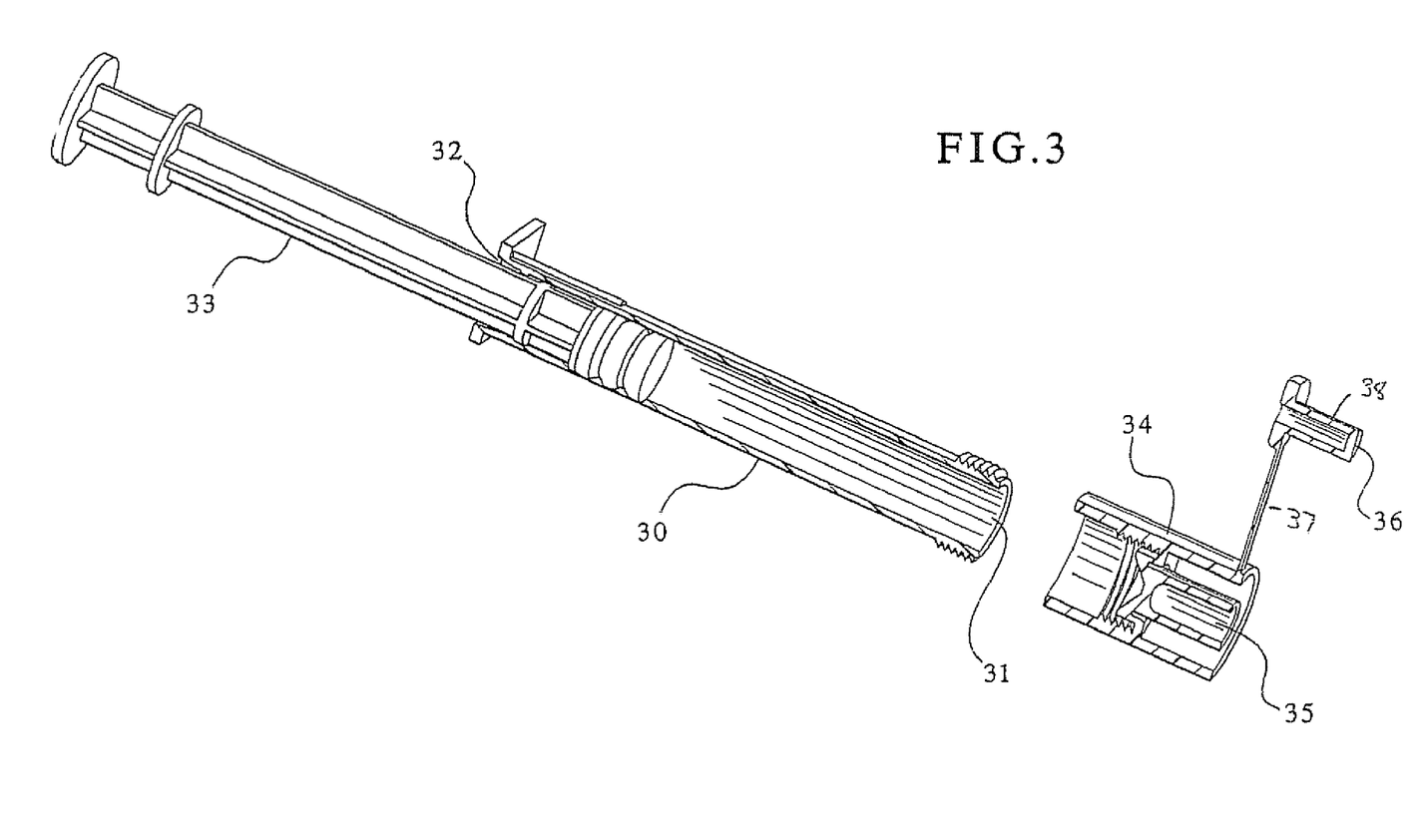
FIG. 3 illustrates a schematic view of yet another device of the present invention.

FIG. 3 shows another medical device of the present invention that allows for mixing of chemically reactive substances, and ultimately the extrusion of the final composition resulting from the chemical reaction between or among those substances. The medical device features a syringe assembly with a hollow tube 30 that has a forward opening 31 and a rear opening 32 and a plunger 33. A removable cap 34 can be used to cover the forward opening. The removable cap 34 can be secured over the forward opening 31 preferably by mating threads. The removable cap 34 additionally contains a female leur port 35 into which a male leur tip 38 can be inserted. The port has a removable cover 36 attached by a retaining member 37.

Figure 4A:
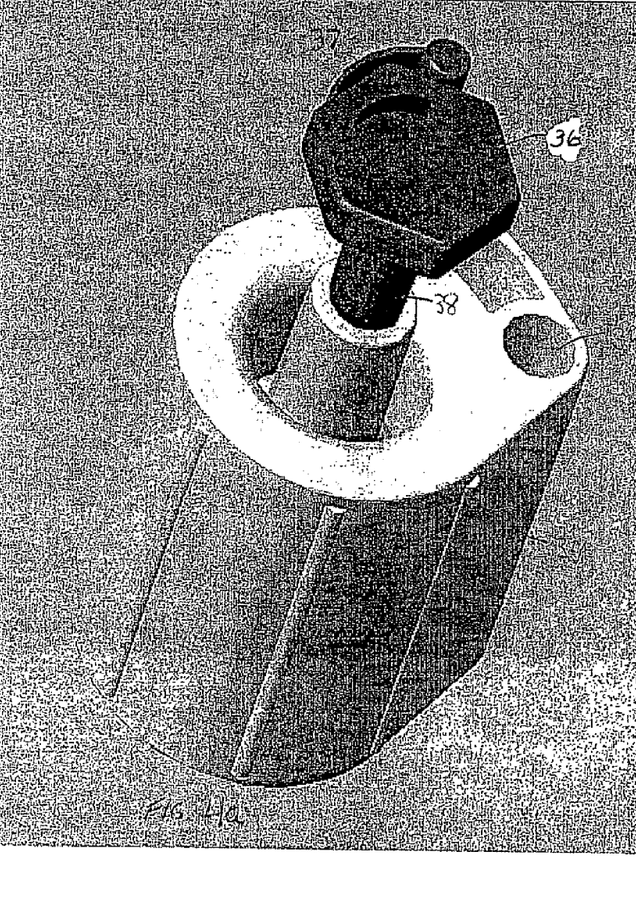
FIGS. 4a-c illustrate perspective views of yet another device of the present invention featuring a cap which has a luer tip that can be moved into a docking position.
Figures 4B, 4C:
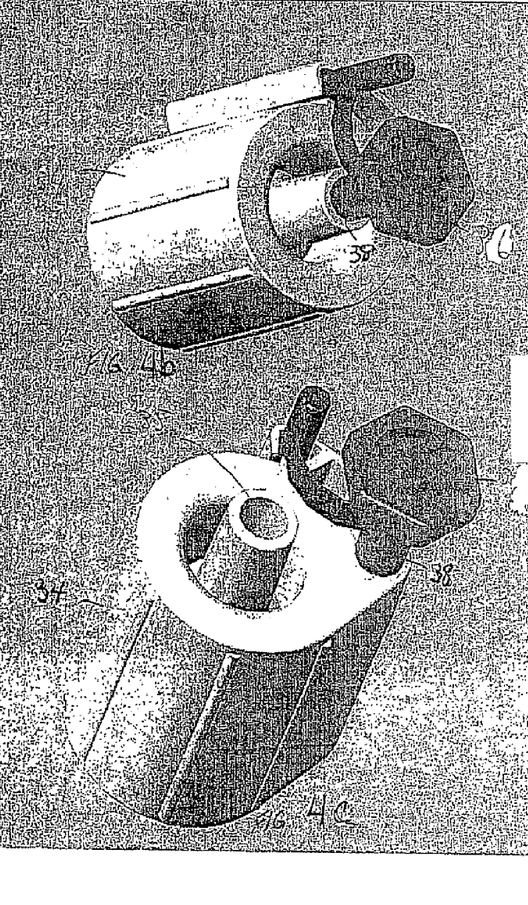

FIGS. 4a-c shows an alternative embodiment of the device of FIG. 3 having the cap 34 with the removable cover 36 and the retaining member 37 with a docking port 39. In this device, the male luer tip 38 can be removed by lifting the male luer tip 38 from the female luer 35 and moving through an angle of approximately 30+ and inserting into a docking port 39 (FIG. 4c) (defining a docking position) which is preferably shaped like a female luer. This design is advantageous since the docking position increases the overall safety of the device and simplifies handling. Moreover, the design facilitates automation of the filling process.

Another advantage of the design of the syringe body of the present invention is that the pitches are on the external side of the syringe body and not the inside. This results in there being no restriction of the diameter of the syringe body and that the composite can be extruded without scratching or destroying its shape. Therefore, the diameter of the composite equals the diameter of the syringe.

III. Methods of Using the Devices

All of the devices of the present invention can be used to mix and extrude any substances that, when mixed, produce a medically useful composition. However, all of the devices are especially suitable for the mixing and extrusion of bone replacement materials such as those comprising MBCP and fibrin glue. As stated previously, thrombin provides the catalyst that, when reacted with fibrinogen, causes fibrinogen to form fibrin monomers. It is therefore necessary that the thrombin and fibrinogen be segregated within the devices until the time at which their mixing is desired. The devices of the present invention allow for such segregation of the chemically reactive components.

The three-container device shown in FIG. 1 can be used to mix and extrude any medically useful composition. However, when it is used to mix and extrude a bone replacement composition such as that resulting from MBCP and fibrin glue, an preferred method of use for the device is as follows.

In a preferred embodiment, fibrinogen can be placed in the first container 10. Thrombin can be placed in the second container 12. MBCP granules can be placed in the third container 14. The first, second, and third containers can be attached via the connector 16. When the practitioner desires to create the bone replacement material, the fibrinogen and the thrombin in the first and second containers 10, 12 can be forced into the connector 16 here they begin the mixing process. These substances are further forced into the third container 14 where they can surround the MBCP granules. Ideally the fibrin glue will penetrate the pores of the MBCP granules, as well as the inter-granular space. After the fibrin glue has mixed with the MBCP granules within the third container, at the desired time, the connector can optionally be disconnected from the third container. The final bone replacement material can then be extruded from the third container for its intended medical purpose. The opening for extrusion can vary depending on the wishes of the practitioner. Standard syringe barrels have a tapered distal end 15. In this regard, it may be desirable to separate the reduced diameter portion or the syringe barrel from a constant diameter portion of the third container 14. The method of separating the reduced diameter portion from the constant diameter portion can include unscrewing one port from the other or breaking one port away from the other along a frangible portion. The screw type system is more desirable than the frangible type as the frangible system can form undesired particulates. Another way to extrude the composite out of the syringe without cutting the leur end may be performed by removing the plunger and pushing the composite out mechanically or with air.

The two-container device shown in FIG. 2 can be used to mix and extrude any medically useful composition. However, when it is used to mix and extrude a bone replacement composition such as that resulting from MBCP and fibrin glue, a preferred method of use for the device is as follows.

In a preferred embodiment, fibrinogen can be placed in the first container 20. For the MBCP component, MBCP granules pre-adsorbed with thrombin, a mixture of MBCP granules adsorbed with thrombin and MBCP granules adsorbed or coated with molecules such as bone morphogenetic proteins (BMP's), or a mix of at least two species of MBCP granules pre-adsorbed with different molecules can be used. These mixtures may be homogeneous or in layers. These MBCP combinations are placed in the second container 22. When it becomes desirable to create the bone replacement material, pressure can be applied such that the fibrinogen in the first container 20 is forced through the connector 24 into the second container 22 where it can react with the thrombin on the pre-coated thrombin MBCP granules. The reaction between the thrombin and the fibrinogen serves to create the fibrin glue that will bind in and around the MBCP granules. At the desired time, the connector 24 optionally can be disconnected from the second container 22. The final bone replacement material can then be extruded from the second container 22 for its intended medical purpose. The opening for extrusion can vary depending on the wishes of the practitioner. Standard syringe barrels have a tapered distal end 21, 23. In this regard, it may be desirable to separate the reduced diameter portion or the syringe barrel from a constant diameter portion of the second container 22. The method of separating the reduced diameter portion from the constant diameter portion can include unscrewing one port from the other or breaking one port away from the other along a frangible portion. The screw type system is more desirable than the frangible type as the frangible system can form undesired particulates.

The devices shown in FIGS. 1 and 2 can additionally be used in a manner whereby the contents are placed in the respective containers to be stored at room temperature or quickly frozen or freeze dried for later use. For this kind of application, it may be desirable to store the loaded/frozen device in a blister pack for later use.

As noted previously, the containers that compose the devices shown in FIGS. 1 and 2 are preferably syringes. When typical syringes are used, it is assumed that the contents for the various containers can be transferred among the containers and/or connector via the action of the syringe plunger that is driven manually by hand-force. However, even when syringes are used, it may be desirable to use automated techniques to depress the syringe plungers. Moreover, it non-syringe containers are employed, then the practitioner may use other methods to transfer the container contents between and among the containers and/or connector. Such schemes for transferring contents will depend on the type of container/connector employed, and may include, for example, gravity.

The one-container device shown in FIG. 3 can be used to mix and extrude any medically useful composition. However, when it is used to mix and extrude a bone replacement composition such as that resulting from MBCP and fibrin glue, a preferred method of use for the device is as follows.

In a preferred embodiment, initially, the plunger is retracted. The screw cap 34 is removed to expose the barrel 30 of the device. The device is then tilted such that the uncapped barrel end is pointed upward. The device is filled with a specific quantity of fibrinogen and then frozen (with the uncapped barrel remaining facing upward) at a temperature of approximately 0° C. or below, preferably −18° C., and most preferably at −80° C. After the fibrinogen is frozen, thrombin-coated MBCP granules are placed in the device barrel immediately atop the frozen fibrinogen. The screw cap is quickly attached and the entire device is again stored at approximately 0° C. or colder, preferably −18° C. When ready for use, the device (and contents loaded therein) can be removed from the freezer and allowed to thaw at room temperature. After thawing, the plunger is pushed to force the fibrinogen solution to fill out the micro, macro, and inter granular spaces of the thrombin adsorbed HA granules. The screw cap is removed and the composition can be extruded. In this sense the device is an "All in One" device since the fibrinogen, thrombin and MBCP granules are all packed within the same syringe.

While the above is a preferred method of use, it is possible to vary the placement of the fibrinogen and thrombin adsorbed MBCP granules within the device. Moreover, granules coated or adsorbed with other molecules such as BMP's can be used instead of regular MBCP granules, as well as mixtures of different coated granules. It is also possible to have a frozen or freeze dried layer of fibrinogen, a frozen or freeze dried layer of thrombin, gelatin and a layer MBCP granules, placed in any order or in any combination within the same syringe. For example, the first layer may be freeze dried thrombin and the second layer may be gelatin. Alternatively, the first layer may be BMP's frozen or freeze dried with the second layer being thrombin adsorbed MBCP granules. In yet another example, layer 1 will be thrombin frozen or freeze dried and layer 2 will be gelatin beads, fibers or powders, or collagen, alginate and any biopolymers synthetic or natural. Still yet another example includes a first layer being fibrinogen frozen or freeze dried and a second layer which will be a mix of thrombin adsorbed MBCP granules and BMP adsorbed MBCP granules. Frozen water can be used as a separator to avoid diffusion of molecules between the layers of the reactive agents. The second layer being homogeneously distributed or organized in separate but consecutive layers. In examples where the layers are freeze dried, the surgeon will reconstitute by aspirating with a liquid which can be water, buffer, polymerizing polymer synthetic or natural, and double component polymerizing material such as fibrin, plasma, and bone marrow with selected or all stem cells.

It is also possible to use three or more layers within the same container. In such an example, layer 1 will be fibrinogen frozen or freeze dried, layer 2 will be thrombin frozen or freeze dried, and layer 3 will be MBCP granules or granules adsorbed with other molecules such as BMP, or a mixture thereof. In a four layer configuration, layer 4 can be any liquid frozen or freeze dried. As with all of the other examples discussed in detail above, these layers may be placed in any sequence without affecting the overall operation of the device.

As shown in FIG. 3, the removable cap 34 of this device additionally contains a female luer port 35 into which a male luer tip can be inserted. The port has a removable cover 36. The purpose of the leur port is to facilitate the convenient injection and extraction of substances in and out of the device when the screw cap is in place. The cap 34 can optionally have a retaining member 37 to hold the removable cover 36 when the cover 36 is not inserted in the port 35.

One advantage of the device shown in FIG. 3 is that it allows for sedimentation-free delivery of bone replacement materials. Thus, the liquid is injected into the granule layer and not the opposite. The liquid may be water, buffer, polymerizing material such as fibrin, plasma, bone marrow with selected of all stem cells, rich platelet plasma, autologous fibrinogen, recombinant proteins or any combination thereof. The liquid or liquids fill out voids in the form of micro, macro, or inter granular spaces of MBCP granules without disturbing or inducing motion of the MBCP granules, only displacing the equivalent volume of air, therefore the MBCP granules do not move. Moreover, it additionally allows for air-free delivery, which contrasts with the devices shown in FIGS. 1 and 2, both of which may trap air in the container prior to polymerization.

The above devices are advantageous because they allow for mixing and extrusion to occur in a single device. Moreover, they are especially advantageous when used for mixing and delivery of bone replacement materials. In this regard, when, for example, these devices are used to mix fibrin glue with MBCP granules, various aspects of the mixing process are optimized. Fibrin polymerizes in the inter- and intra- granular spaces of the MBCP granules, insuring a homogeneous distribution of fibrin in the mixture. This leads to a beneficial 3-D structure of fibrin that is protected from shear stress providing a network for cell ingrowth. Moreover, because of the volumetric nature of the device components, there is no excess of fibrin glue and no risk of void volume formation once fibrin is degraded. Additionally, the problem of settlement of large granules when mixed with solutions is avoided. Furthermore, mechanical properties such as break at compression and Young modulus should be unchanged, while elasticity of the mixture should be improved.

Another advantage of the devices of the present invention is the optimization of the injectibility factor of the composite. Calcium phosphate cement have been in clinical use for at least 10 years. When calcium phosphate cement (CPC) is injected into a bone defect with a conventional syringe and a needle, it has been observed that quantities of the cement stay in the syringe. The only thing that can be pressed out in some cases is a small amount of liquid (phase separation). This phenomenon is called filter-pressing. Filter pressing can be explained as follows. When a cement paste is injected through a needle into a defect, a pressure, $\Delta pn$ is applied on the paste. It the applied pressure is high enough to press the mixing liquid through the cement particles, filter pressing will occur. Therefore, the ability of a cement to sustain filter pressing can be defined as the ratio between the pressure required to press the liquid through the particles divided by the pressure required to push the cement through the needle ($\Delta pn$). (M Bohner, Proceedings of the $17^{th}$ European Conference on Biomaterials reference:P124). This ratio "$\lambda$" is called the injectability factor, where $\lambda=\Delta p/\Delta pn$. The injectability factor is defined and used to describe the ability of the paste for cement of composite in our case to prevent filter pressing, in other words to improve its inejctability. The injectability based on the two definitions above, is independent from: size of the granules used, shape and porosity of the granules (compaction effect), temperature of use, kinetic of the polymerization of fibrin, time after mixing, force required to inject the composite (extrusion force), and needle (needleless).

A good cement or composite injectability can only be reached when filter pressing does not occur i.e. when $\Delta p$ is very low, which means when $\lambda$ is large. Other authors define the injectability based on the calculation of the weight percentage of the extruded paste to the total mass of cement paste. A. Almirall, Proceedings of the $17^{th}$ European Conference on Biomaterials reference:T70. By this definition, the present invention maximizes injectibility since 100% of the composite weight is extruded. Thus, the device of the present invention does not suffer from the filter pressing effect. Indeed, when there is filter pressing, liquid will percolate through the solid particle and exit the syringe or device, which means that the homogeneity of the composite extruded will be different. This will result in the first portion of the composite extruded having more liquid than the composite at the end. Based on one design of the syringe body in accordance with the present invention, the opening has the same diameter as the internal diameter of the body of the syringe. Therefore, no filter pressing is observed and a good injectability is achieved because of the design features of the devices of the present invention. These features include the exit equaling the internal diameter of the syringe, a luer end that can be unscrewed, and the lubricating effect of the water and fibrin glue distributed in the granules bed.

In addition, it has been observed that thrombin is adsorbed on polymers such as PVC or polyolefin, polyethylene, and polypropylene such as the materials used for fabricating commercially available syringes. Therefore, it is possible to adsorb thrombin on the inner wall of a syringe which will then be loaded with MBCP granules. The device containing the MBCP granules may then be connected to a syringe containing fibrinogen, which is injected into the MBCP granule layer.

As discussed above, the volumetric requirements of mixing the mineral component with the glue components are very predictable when employing the devices of the present invention for mixing. In this regard, the relative amounts of mineral granules and fluid glue components are governed by the equation $V_{MBCP}=V_{MBCP}+V_{GLUE}$. This means that, for example, when mixed in a syringe, the final volume of the mineral-glue composition will be equal to the original volume of the mineral component when alone. In this regard, when mixed in a syringe the liquid will enter the pores of the mineral component as well as surround the extra-granular spaces around the granules.

In a preferred embodiment, the bone replacement material can include from about 10% to about 100% mineral and from about 30% to about 100% glue (e.g., fibrin glue). The exact compositions used will depend on if the mineral is mixed of used in combination with other granules and if the mineral is hydrated before being mixed with the fibrin.

The devices and methods of the present invention can be utilized for numerous applications, including those associated with osteopathic uses. For example, a professional can use equipment known in the art to initially scan the target bone to determine the extent of a given defect and, if necessary, the volume of the defect that potentially requires treatment with a bone replacement composition. In addition, the surgeon can use software in order to chose the MBCP based on the application, since different types of MBCP have different skeletal porosity, density and shape. Normally, a surgeon will want to pack as much of the bone defect with an optimal mass MBCP. If the bone defect volume is Vd the present invention allows mixing MBCP with fibrin as per the following equation: $V_{MBCP} = V_{MBCP} + V_{FIBRIN} = V_{COMPOSITE}$ wherein after the surgeon completes application of the composite, Vd will essentially equal Vcomposite. As the volume of the fibrin is relayed to the skeletal porosity, the surgeon using the software can make the choice for a particular MBCP material having its specifications and determine the volume of fibrin required to fully immerse the MBCP.

Of course, the exact mixture of components of the mixture will vary depending on the type of bone and the nature of the bone defect. In this regard, the mixture can be predicted and manipulated to include mineral granules of varying porosities and glues that have varying bonding strengths and polymerization rates.

After mixing and extruding the bone replacement material by using the devices and methods of the present invention, the material can be applied to the target bone and molded accordingly. Another feature of the present invention is described as follows, after mixing the composite is freeze dried in the syringe, capped, and packaged in a rigid blister.

In addition to the above, a different diameter of syringe will provide the surgeon with a different diameter of extruded material. The practitioner can then use a surgical drill to drill holes in the target bone and plug the holes using appropriate "off the shelf" bone replacement material as cylinders, carrots or plugs, edges, and squares. These "off the shelf" materials could be presented in a device having the shape of the material and equipped with a luer to be connected with a syringe that contains another liquid or liquids to be injected. The plugs can be textured on their outer surfaces to reduce surface contact for ease of insertion. However, it is desired to have as much surface contact as reasonably possible with the bone wall defect.

Figure 5:
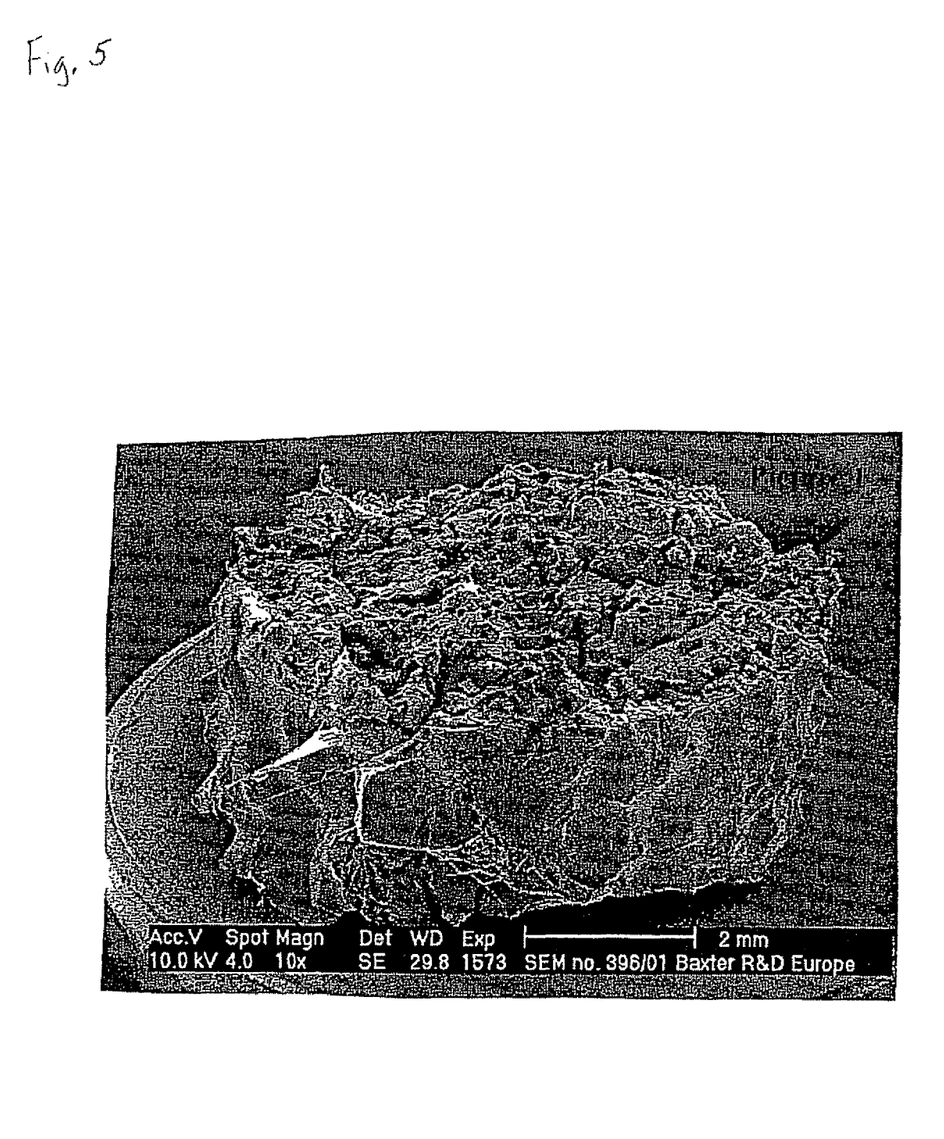
FIG. 5 is a scanning electron micrograph of a cross-section of a sample of bone replacement material mixed and extruded using a device of the present invention.
Figure 6:
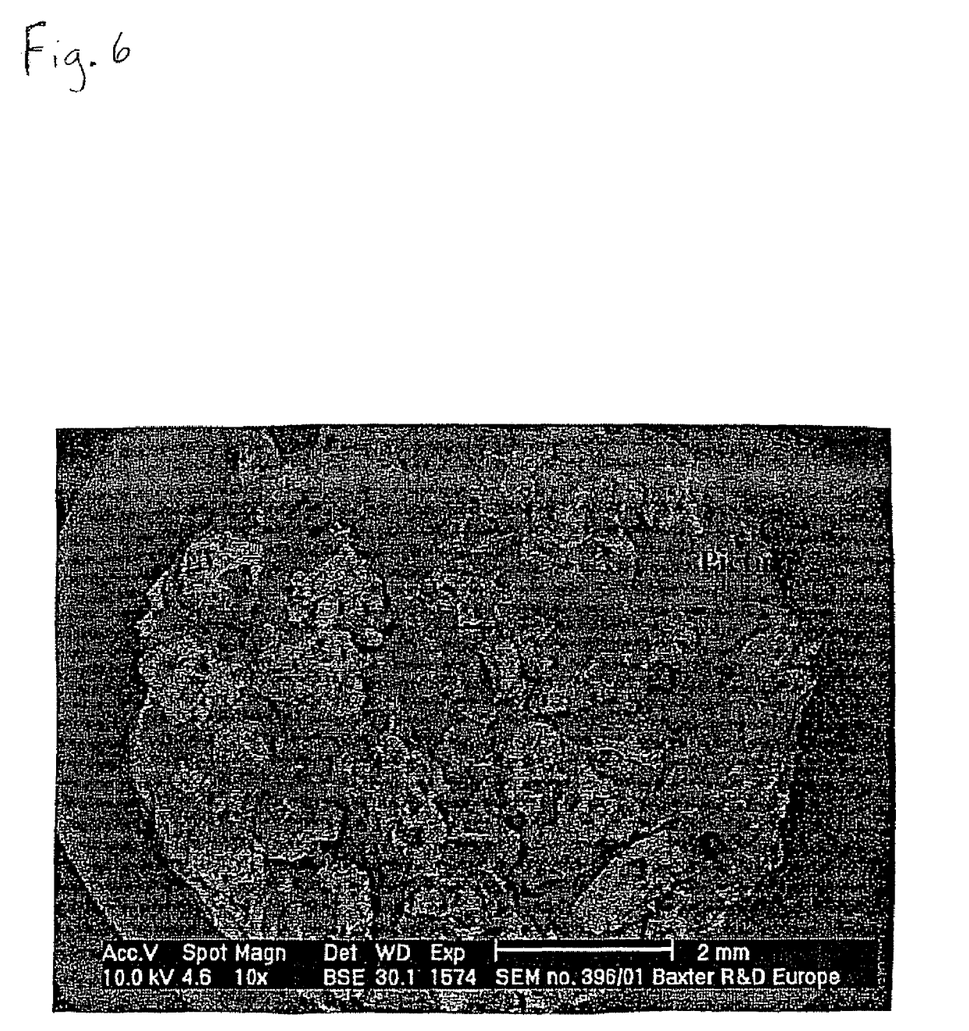
FIG. 6 is a scanning electron micrograph of a cross-section of an additional sample of bone replacement material mixed and extruded using a device of the present invention.

Turning now to FIG. 5, a scanning electron micrograph of a cross-section of a sample of bone replacement material mixed and extruded using a device of the present invention is shown. The bone replacement material consists of MBCP/fibrin glue. A fibrin membrane is formed around the MBCP/fibrin mixture. FIG. 6 is a scanning electron micrograph of a cross-section of another sample of bone replacement material mixed and extruded using a device of the present invention. Dark gray areas show the fibrin polymer which is present in all inter-granular spaces as well as inside the pores of the granules. The light gray areas represent surface areas of the MBCP granules.

EXAMPLES

Example 1

Mixing and Extrusion in a Three-Container Device 1.45 mL fibrinogen (100 mg/mL) was placed in a first syringe barrel as depicted in FIG. 1. 1.45 mL thrombin (4 IU/mL) was placed in a second syringe barrel as depicted in FIG. 1. The first and second syringe barrels were part of a dual syringe assembly sold under the trade name of DUOFLO (Hemaedics). In addition to the above, the DUPLOJECT system available from Baxter Bioscience may also be used. 2.0 g MBCP was placed in a third syringe barrel as depicted in FIG. 1. The three syringes were connected using a Y-shaped female-female luer connection piece. The medical device was tilted such that the MBCP-containing syringe barrel pointed downward toward the syringe barrels containing fibrinogen and thrombin. Using hand pressure, the fibrinogen and thrombin were forced upward through the connector and into the MBCP-containing syringe. After polymerization, the syringe containing the MBCP-fibrin glue composition was disconnected from the connector and was cut at its distal end. The MBCP-fibrin glue mixture was then extruded by applying hand pressure to the syringe plunger.

Example 2

Mixing and Extrusion in a 2-Container Device

MBCP granules were pre-coated with thrombin. Coating with thrombin was achieved using the following procedure. 1.0 g of MBCP granules was placed in a 3.0 mL syringe. The MBCP-containing syringe was connected to a syringe containing 2.0 mL thrombin solution (10 IU/mL in $CaCl_2$ 1.5 mM (concentration of $CaCl_2$ can be increased to up to 40 mM); syringe not shown in FIG. 2). 1.5 mL thrombin solution was injected into the MBCP-containing syringe. The thrombin solution was re-aspirated back from the MBCP-containing syringe, 0.9 to 1.0 mL remains into the MBCP. The MBCP granules may optionally be washed with a $CaCl_2$ 2.5 mM solution, depending on the clotting time or polymerization time required. 1.5 mL of fibrinogen at 50 mg/mL was placed into a second syringe as depicted in FIG. 2 and connected to the thrombin adsorbed MBCP containing syringe. The medical device was tilted such that the thrombin adsorbed MBCP-containing syringe barrel pointed downward toward the syringe barrel containing fibrinogen. Using hand pressure, the fibrinogen was forced upward through the connector and into the thrombin adsorbed MBCP-containing syringe. After polymerization, the syringe containing the MBCP-fibrin glue composition was disconnected from the connector and was cut at its distal end. The MBCP-fibrin glue mixture was then extruded by applying hand pressure to the syringe plunger.

Example 3

Mixing and Extrusion in a 1-Container Device

Initially, the plunger of the single-container device as shown in FIG. 3 was retracted. The screw cap was removed to expose the barrel of the device. The device was then tilted such that the uncapped barrel end pointed upward. The device was filled with 1.5 mL fibrinogen (50 mg/mL) and frozen (with the uncapped barrel remaining facing upward) at a temperature of approximately −18° C. or below. After the fibrinogen was frozen, 1.0 g of the thrombin-adsorbed MBCP granules of Example 2 were placed in the device barrel immediately atop the frozen fibrinogen. The screw cap was quickly attached and the entire device was stored at approximately −18° C. or below. When ready for use, the device was removed from the freezer and allowed to thaw at room temperature or at 37° C. After thawing, the melted fibrinogen solution was pushed with the plunger to fill out the skeletal porosity of the granules to mix with the thrombin-adsorbed MBCP. It should be noted that 1.5 mL of a solution, in this case, fibrinogen can fill out the porosity of 1.0 g of MBCP. The screw cap was then removed and the composition was extruded.

Example 4

Mixing and Extrusion Using a Hydration Step

Hydration with water was achieved using the following procedure. 1.0 g of MBCP granules were placed in a 3.0 mL syringe. The MBCP-containing syringe was connected to a syringe containing 2.0 mL of water. Water was injected into the MBCP-containing syringe. The excess of water was re-aspirated back from the MBCP-containing syringe, 0.9 to 1.0 mL remains into the MBCP. The syringe containing the excess of water is discarded. 0.5 mL fibrinogen (100 mg/mL) was placed in a first syringe barrel as depicted in FIG. 1. 0.5 mL thrombin (4 IU/mL) was placed in a second syringe barrel as depicted in FIG. 1. The first and second syringe barrels were part of a dual syringe assembly sold under the trade name of DUOFLO (Hemaedics). In addition to the above, the DUPLOJECT system available from Baxter Bioscience may also be used. Hydrated MBCP (1.0 g) is placed in a third syringe barrel as depicted in FIG. 1. The three syringes were connected using a Y-shaped and the female-female luer connection piece. The medical device was tilted such that the MBCP-containing syringe barrel pointed downward toward the syringe barrels containing fibrinogen and thrombin. Using hand pressure, the fibrinogen and thrombin were forced upward through the connector and into the MBCP-containing syringe. After polymerization, the syringe containing the MBCP-fibrin glue composition was disconnected from the connector and was cut at its distal end. The MBCP-fibrin glue mixture was then extruded by applying hand pressure to the syringe plunger.

Example 5

Mixing and Extrusion Using a Water Gap

Initially, 1.0 ml of the first reagent fibrinogen (100 mg/mL) was poured into the single-container device as shown in FIG. 3 and frozen at a temperature of approximately −18° C. A non-reactive substance which in this example was pure water was then poured over the frozen fibrinogen layer and the syringe was frozen again at a temperature of approximately −18° C. The amount of water used was enough to create an interface of at least 1 mm between the first and second reactant. The device was then filled with 1.0 at 4 IU/mL of a second reagent thrombin which was poured over the non-reactive layer of frozen water. During the freeze drying process, the water was then sublimated leaving a void between the two unreacted dried reagents. Before using, the syringe was then hydrated by aspirating a diluent or buffer causing the two reagents to react forming a composition. The screw cap was then removed and the composition was extruded.

From the foregoing, it will be observed that numerous variation and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention is claimed as follows:

1. A medical device for mixing and extruding a bone replacement material comprising:

a syringe comprising a single hollow cylindrical chamber having an upward opening and a downward opening, and a movable member configured to slide within the chamber;

a first chemically reactive substance that is located within the syringe, said substance being liquid above approximately zero degree centigrade and being maintained in a frozen state at a first temperature and disposed at a lower location; and a second chemically reactive substance that is solid at room temperature and located in the syringe atop the first substance without mixing with the first substance when the syringe is maintained at the first temperature, such second chemically reactive substance having a plurality of pores;

wherein, the first substance thaws to a liquid state upon the syringe being exposed to room temperature such that actuation of the movable member pushes the thawed first chemically reactive substance upward into the pores of the second chemically reactive substance, the volume of the first substance being sufficient to immerse the second substance to allow for mixing of such first and second substances within the hollow cylindrical chamber prior to extrusion through the upward opening.

2. The medical device of claim 1 wherein the syringe includes a removable cap that is attached to the forward opening.

3. The medical device of claim 1 wherein the movable member is slidably mounted within the chamber.

4. The medical device of claim 1 wherein the first chemically reactive substance includes fibrinogen.

5. The medical device of claim 1 wherein the second substance includes thrombin.

6. The medical device of claim 5 wherein the second substance includes at least one mineral substance.

7. The medical device of claim 6, wherein the mineral substance is selected from the group consisting of hydroxyapatite, calcium carbonate, calcium sulfate, biphasic materials constituted of hydroxyapatite and calcium based minerals, ion substituted hydroxyapatite, polarized hydroxyapatite, and blend corn starch with hydroxyapatite.

8. The medical device of claim 6 wherein the thrombin is adsorbed onto the mineral substance prior to placement in the syringe.

9. The medical device of claim 1 wherein the movable member is a plunger having two stop ends for preventing the plunger from being pushed out of the syringe when a composite is extruded.

10. The medical device of claim 7 wherein the mineral substance includes MBCP.

11. The medical device of claim 1 wherein the volume of the second chemically reactive substance is substantially equal to the volume of the first and second chemically reactive substances.

12. The medical device of claim 1 wherein the second chemically reactive substance has a porosity of about 80.5%.

13. The medical device of claim 1, wherein the syringe comprises a single movable member configured to slide within the chamber.

14. The medical device of claim 13, wherein the single moveable member comprises a single piston disposed in the single hollow cylindrical chamber and a pusher member with a first end attached to the single piston and a second end depending from the single hollow cylindrical chamber.

* * * * *